(12) United States Patent
Slager

(10) Patent No.: US 8,246,576 B2
(45) Date of Patent: Aug. 21, 2012

(54) METHOD AND APPARATUS FOR DELIVERY OF A THERAPEUTIC AGENT WITH AN EXPANDABLE MEDICAL DEVICE

(75) Inventor: Joram Slager, St. Louis Park, MN (US)

(73) Assignee: SurModics, Inc., Eden Prairie, MN (US)

( * ) Notice: Subject to any disclaimer, the term of this patent is extended or adjusted under 35 U.S.C. 154(b) by 3 days.

(21) Appl. No.: 12/774,954

(22) Filed: May 6, 2010

(65) Prior Publication Data

US 2010/0292668 A1 Nov. 18, 2010

Related U.S. Application Data

(60) Provisional application No. 61/179,164, filed on May 18, 2009.

(51) Int. Cl.
*A61M 31/00* (2006.01)
*A61M 29/00* (2006.01)

(52) U.S. Cl. ............. 604/103.02; 604/96.01; 604/99.01; 604/509; 604/97.01

(58) Field of Classification Search .. 604/96.01–103.14, 604/265, 509
See application file for complete search history.

(56) References Cited

U.S. PATENT DOCUMENTS

| | | | |
|---|---|---|---|
| 4,638,045 A | | 1/1987 | Kohn et al. |
| 5,102,402 A | * | 4/1992 | Dror et al. ............... 604/265 |
| 5,304,121 A | * | 4/1994 | Sahatjian ................ 604/509 |
| 5,397,307 A | | 3/1995 | Goodin |
| 5,414,075 A | | 5/1995 | Swan et al. |
| 5,558,642 A | | 9/1996 | Schweich, Jr. et al. |
| 5,637,460 A | | 6/1997 | Swan et al. |
| 5,980,948 A | | 11/1999 | Goedemoed et al. |
| 6,278,018 B1 | | 8/2001 | Swan |
| 6,623,452 B2 | | 9/2003 | Chien et al. |
| 6,703,040 B2 | | 3/2004 | Katsarava et al. |
| 7,438,710 B2 | | 10/2008 | Anderson et al. |
| 2003/0065355 A1 | | 4/2003 | Weber |
| 2003/0195611 A1 | | 10/2003 | Greenhalgh et al. |
| 2003/0211135 A1 | | 11/2003 | Greenhalgh et al. |
| 2004/0051201 A1 | | 3/2004 | Greenhalgh et al. |
| 2005/0187605 A1 | | 8/2005 | Greenhalgh et al. |
| 2005/0255142 A1 | | 11/2005 | Chudzik et al. |
| 2006/0018948 A1 | | 1/2006 | Guire et al. |
| 2006/0200232 A1 | | 9/2006 | Phaneuf et al. |
| 2007/0026037 A1 | | 2/2007 | Kloke et al. |
| 2007/0048351 A1 | | 3/2007 | Lunn |

(Continued)

OTHER PUBLICATIONS

Birnbaum, Duane T. et al., "Microparticle Drug Delivery Systems", Chapter 6, *Drug Delivery Systems in Cancer Therapy* 2003, pp. 117-135.

(Continued)

*Primary Examiner* — Kevin C Sirmons
*Assistant Examiner* — Bradley Thomas, Jr.
(74) *Attorney, Agent, or Firm* — Pauly, Devries Smith & Deffner, L.L.C.

(57) ABSTRACT

Described herein is a medical device that has a collapsed configuration and an expanded configuration wherein one or more polymeric network layers are applied to the substrate and microparticles embedded in the polymeric network. The polymeric network layer or layers is/are configured to retain the microparticles when the device is in a collapsed configuration and to release the microparticles when the device is in an expanded configuration. Methods for delivering a therapeutic agent using the device and making the device are also disclosed.

9 Claims, 5 Drawing Sheets

U.S. PATENT DOCUMENTS

| | | |
|---|---|---|
| 2007/0065481 A1 | 3/2007 | Chudzik et al. |
| 2007/0155906 A1 | 7/2007 | Hissink et al. |
| 2007/0218102 A1 | 9/2007 | Chudzik et al. |
| 2007/0260054 A1 | 11/2007 | Chudzik |
| 2008/0220054 A1 | 9/2008 | Shastri et al. |
| 2009/0030504 A1 | 1/2009 | Weber et al. |
| 2009/0043276 A1 | 2/2009 | Weber et al. |
| 2009/0081276 A1 | 3/2009 | Alsberg et al. |
| 2009/0227946 A1* | 9/2009 | Kangas ............... 604/96.01 |
| 2010/0076377 A1* | 3/2010 | Ehrenreich et al. ...... 604/103.08 |
| 2010/0076401 A1* | 3/2010 | Von Oepen et al. .......... 604/509 |

OTHER PUBLICATIONS

"Electrospinning", From *Wikipedia, the free encyclopedia* http://en.wikipedia.org/wiki/Electrospinning, downloaded Mar. 19, 2009; pp. 1-3.

Kumar, Majeti N.V.R., "Nano and Microparticles as Controlled Drug Delivery Devices", *J. Pharm Pharmaceut Sci*, 3(2) 2000, pp. 234-258.

Renkin, Eugene M., "Filtration, Diffusion, and Molecular Sieving Through Porous Cellulose Membranes", Nov. 20, 1954, pp. 1-19.

* cited by examiner

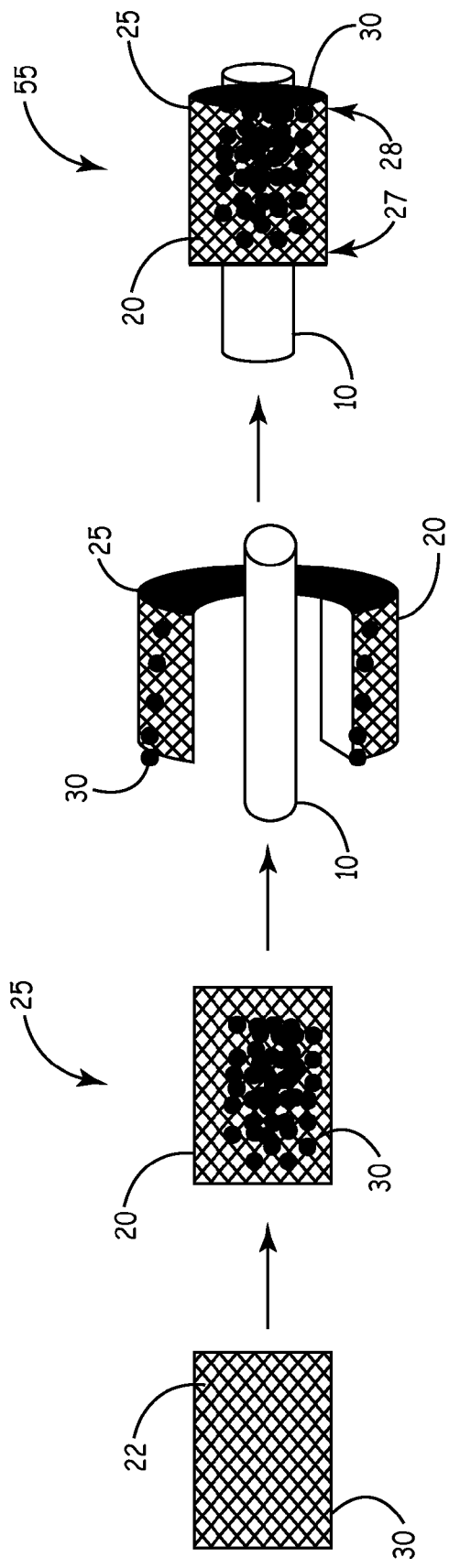

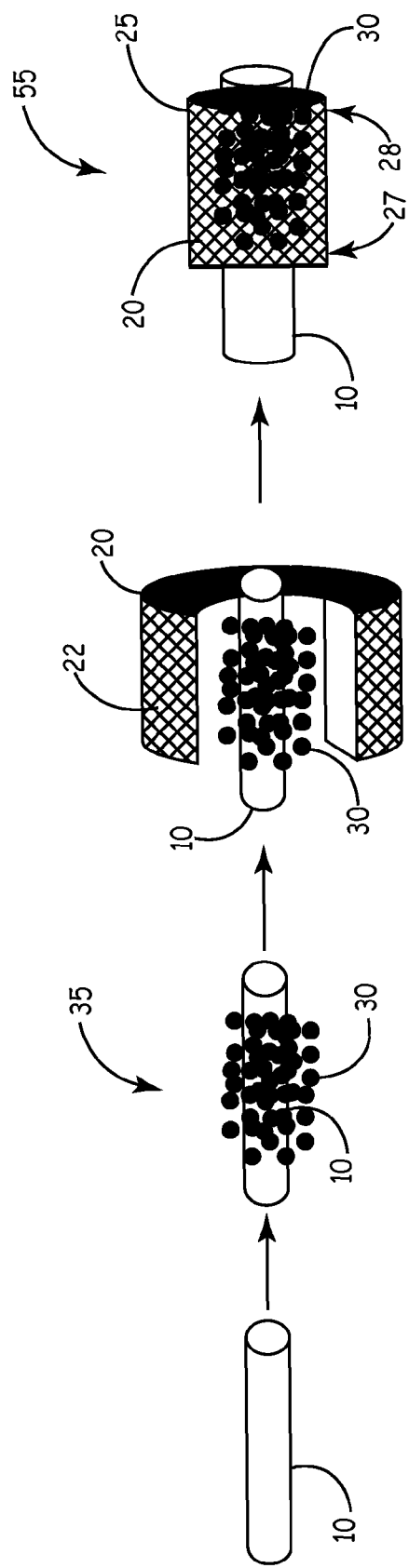

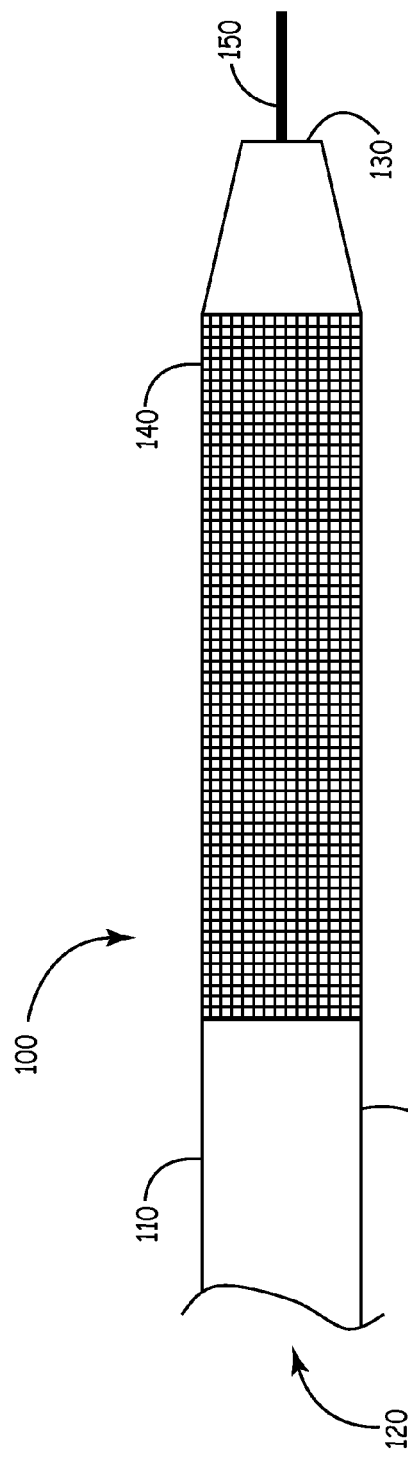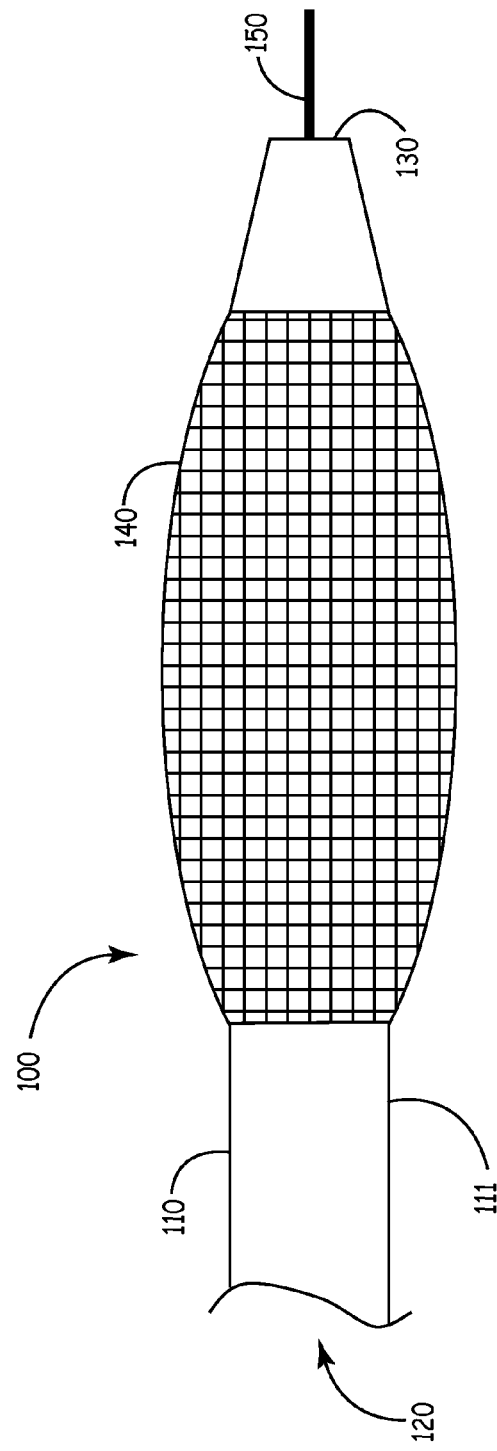

METHOD AND APPARATUS FOR DELIVERY OF A THERAPEUTIC AGENT WITH AN EXPANDABLE MEDICAL DEVICE

This application claims the benefit of U.S. Provisional Application No. 61/179,164, filed May 18, 2009, the content of which is herein incorporated by reference in its entirety.

FIELD OF THE INVENTION

The present invention relates to medical devices that are capable of releasing one or more therapeutic agents. In particular, the present invention relates to expandable medical devices that are capable of releasing one or more therapeutic agents.

BACKGROUND OF THE INVENTION

The vascular system of the human is subject to blockage due to plaque within the arteries. Partial and even complete blockage of arteries by the formation of an atherosclerotic plaque is a well known and frequent medical problem. Frequently, such blockage occurs in the coronary arteries. Such blockages may be treated using atherectomy devices, which mechanically remove the plaque; hot or cold lasers, which vaporize the plaque; stents, which hold the artery open; and other devices and procedures designed to increase blood flow-through the artery.

One common procedure for the treatment of blocked arteries is percutaneous transluminal coronary angioplasty (PTCA), also referred to as balloon angioplasty. In this procedure, a catheter having an inflatable balloon at its distal end is introduced into the coronary artery, the uninflated balloon is positioned at the stenotic site, and the balloon is inflated. Inflation of the balloon disrupts and flattens the plaque against the arterial wall, and stretches the arterial wall, resulting in enlargement of the intraluminal passageway and increased blood flow. After such expansion, the balloon is deflated, and the balloon catheter removed. A similar procedure, called percutaneous transluminal angioplasty (PTA), is used in arteries other than coronary arteries in the vascular system. In other related procedures, a small mesh tube, referred to as a stent is implanted at the stenotic site to help maintain patency of the coronary artery. In rotoblation procedures, also called percutaneous transluminal rotational atherectomy (PCRA), a small, diamond-tipped, drill-like device is inserted into the affected artery by a catheterization procedure to remove fatty deposits or plaque. In a cutting balloon procedure, a balloon catheter with small blades is inflated to activate the blades, score the plaque and compress the fatty matter into the artery wall. During one or more of these procedures, it may be desirable to delivery a therapeutic agent or drug to the area where the treatment is occurring to prevent restenosis, repair vessel dissections or small aneurysms or provide other desired therapy.

SUMMARY

Described herein is an expandable medical device that includes an expandable substrate having a collapsed configuration and an expanded configuration, a polymeric network attached to at least a portion of the expandable substrate, and microparticles embedded in the polymeric network. The polymeric network has a first effective pore diameter when the expandable substrate is in a collapsed configuration and the microparticles have an average diameter greater than the first effective pore diameter of the polymeric network such that the microparticles remain entrapped within the polymeric network when the expandable substrate is collapsed and are released from the network when the expandable substrate is in the expanded configuration. Also described is a method for delivering a therapeutic agent from an expandable medical device in which the expandable medical device is inserted or implanted in a patient and the expandable substrate is expanded to the expanded configuration to release the entrapped microparticles. In one embodiment, the polymeric network has a second effective pore diameter when the expandable substrate is in the expanded configuration and the second effective pore diameter is greater than the average microparticle diameter such that the microparticles are released from the network. In another embodiment, at least some of the polymers in the polymeric network break or rupture when the expandable substrate is in the expanded configuration thereby forming one or more openings at one or more locations that are sufficiently large to allow the release of the microparticles from the polymeric network. Also disclosed herein is a method of making the expandable medical device.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

FIG. 3 is a schematic for one method of making an expandable medical device described herein.

FIG. 4 is a schematic for an alternate method of making an expandable medical device described herein.

FIG. 5 is a schematic of a balloon catheter having a collapsed configuration and an expanded configuration.

While the invention is susceptible to various modifications and alternative forms, specifics thereof have been shown by way of example and drawings, and will be described in detail. It should be understood, however, that the invention is not limited to the particular embodiments described. On the contrary, the intention is to second modifications, equivalents, and alternatives falling within the spirit and scope of the invention.

DETAILED DESCRIPTION

Overview

Described herein is an implantable or insertable medical device for the delivery of a therapeutic agent to a location within a patient. In one embodiment, device is configured to provide controlled release of a bioactive agent at a location within a patient for a period of two or more days, one week or more, two weeks or more, up to four weeks or more.

Figures 1A, 1B:
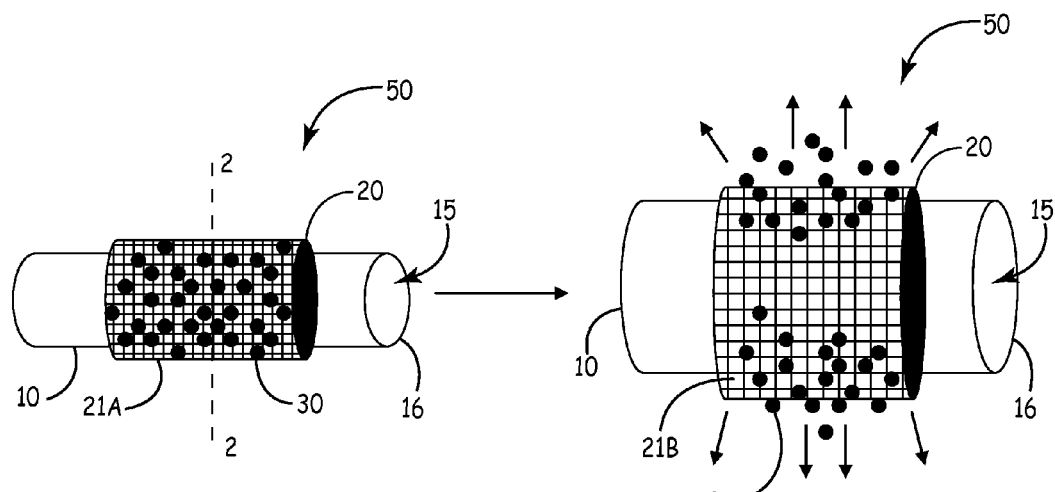
FIG. 1 is a schematic of an expandable medical device described herein.

As shown in FIG. 1, the medical device 50 includes an expandable substrate 10 having a collapsed configuration (FIG. 1A) and an expanded configuration (FIG. 1B), one or more polymeric network layers 20 applied to the substrate 10 and microparticles 30 embedded in the polymeric network 20. The polymeric network layer or layers 20 is/are configured to retain the microparticles 30 when the device 50 is in a collapsed configuration (FIG. 1A) and to release the microparticles when the device 50 is in an expanded configuration (FIG. 1B).

In general, whether or not a polymeric network 20 will retain microparticles 30 is determined by the relative pore size of the polymeric network and microparticle size. However, both the network pores and the microparticles can have irregular shapes and vary in size. Therefore, the term "effective pore diameter" is used herein to characterize particle permeation performance of an electrospun polymeric network. The "effective pore diameter" is defined herein as the maximum diameter of a spherical particle which can pass through the pores in the membrane. Therefore, an electrospun network having an effective pore diameter less than or equal to the average pore diameter of the entrapped or embedded microparticles will tend to retain the microparticles. As used herein, the phrase "tend to retain" the microparticles, means that most or all of the particles remain entrapped in the polymeric network, although some microparticles may be released. In one embodiment, at least about 50% or at least about 75%, and up to about 90% or up to about 100% of the microparticles are retained within the polymeric network. Likewise, an electrospun network having an effective pore diameter that is greater than the average pore diameter of the embedded microparticles will tend to release the microparticles. As used herein, the phrase "tend to release" the microparticles, means that most of the particles are released from the polymeric network over time, although some microparticles may remain entrapped in the polymeric network. In one embodiment, at least about 50% or at least about 75%, and up to about 90% or up to about 100% of the microparticles are released from the polymeric network over time. As used herein, the term "over time" can refer to any suitable time period and can be modified based on the course of desired therapy. It is noted that the average pore diameter of the polymeric network can be greater than the average diameter of the embedded microparticles, but still retain most or all of the microparticles, such that the "effective pore diameter" of the polymeric network is considered to be smaller or less than the average microparticle diameter.

In general, the entrapped or embedded microparticles are released from the polymeric network by a process that includes diffusion. As used herein, the term "diffusion" refers to passive movement of molecules or particles along a concentration gradient, or from regions of higher to regions of lower concentration. In general, the release of the microparticles from the polymeric network will depend on the pore size and the thickness of the polymeric network. In general, the microparticles are entrapped in the polymeric network based on the fact that the microparticles are too large to be able to pass through the pores of the polymeric network.

In one embodiment, the polymeric network 20 has a first effective pore diameter 21A when the expandable substrate 10 is in a collapsed configuration (FIG. 1A) and the microparticles 30 have an average diameter greater than or equal to the first effective pore diameter 21A of the polymeric network such that the microparticles 30 tend to remain entrapped within the polymeric network 20 when the expandable substrate 10 is in a collapsed configuration. In one embodiment, the polymeric network 20 has a second effective pore diameter 21B when the expandable substrate 10 is in an expanded configuration (FIG. 1B), wherein the microparticles 30 have an average diameter that is less than the second effective pore diameter 21B of the networks such that the microparticles 30 tend to be released from the polymeric network 20 when the expandable substrate 10 is in an expanded configuration. In another embodiment (not shown), the polymeric network 20 is configured to rupture upon expansion of the device 50 and release the microparticles. As use herein, the term "rupture" refers to a process in which at least some of the electrospun fibers of the polymeric network break, thereby forming one or more openings at one or more locations in the polymeric network that are sufficiently large to allow the release of microparticles from the polymeric network.

Figure 2:
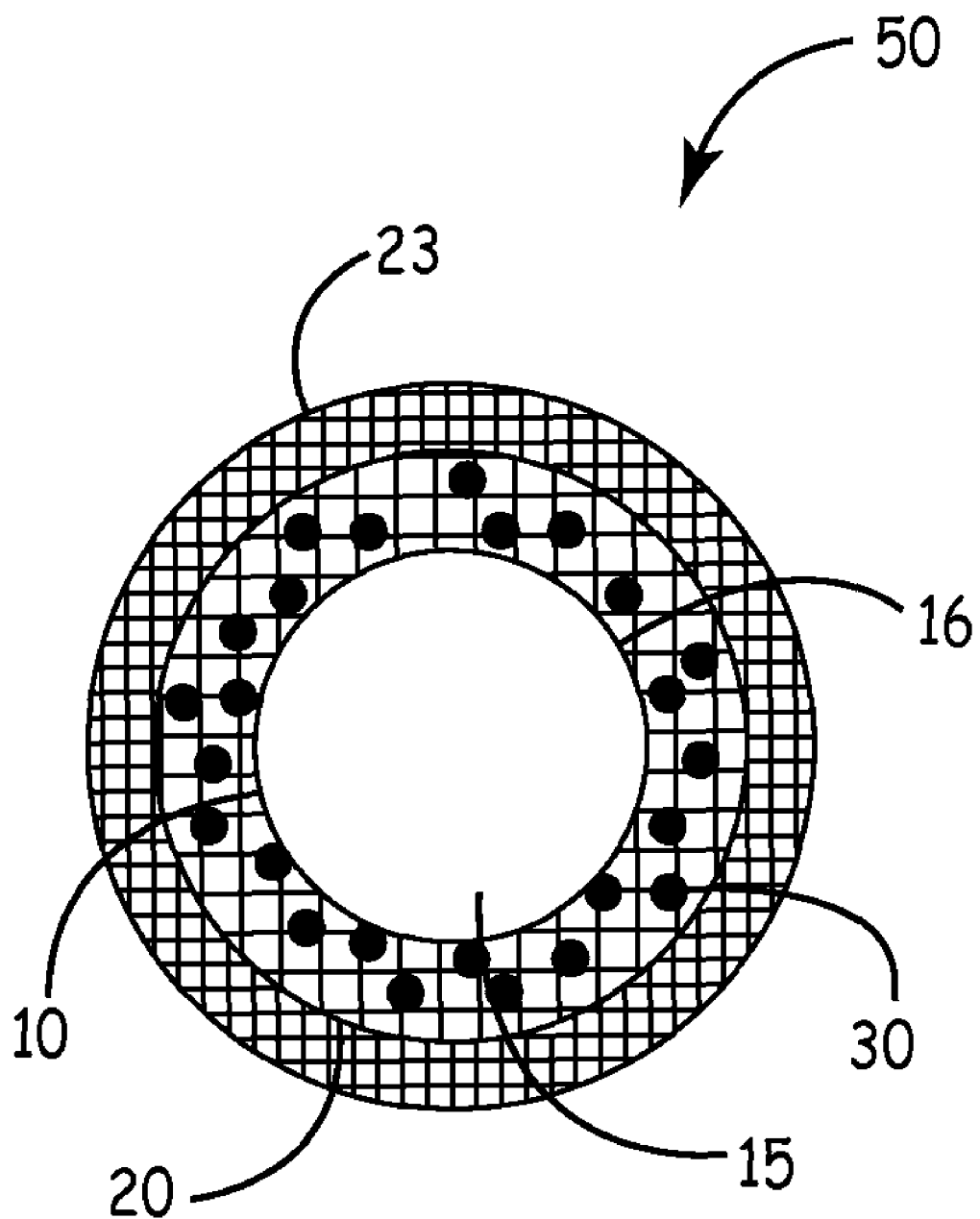
FIG. 2 is a schematic of a cross-section of the expandable medical device of FIG. 1 taken along line 2-2.

FIG. 2 is a cross-sectional view of another embodiment of the implantable medical device shown in FIG. 1 showing the hollow lumen 15 and wall 16 of the expandable medical device 10. In the embodiment shown in FIG. 3, the device 50 includes a first polymeric network layer 20 and a second polymeric network layer 23 applied externally to the first polymeric network layer 20. The second polymeric network layer 23 can also be called a "topcoat" layer.

There are many ways in which the polymeric network 20 can be applied to the expandable substrate 10. In one embodiment, shown schematically in FIG. 3, the network fibers 22 are spun onto a surface to generate a "preformed" polymeric network 20 (step A). Microparticles 30 are embedded in the preformed network 20 (step B) to form a "primed" network 25. As used herein, the term "primed network" refers to a polymeric network with embedded microparticles. Methods for embedding microparticles in an electrospun polymeric network are known, and include spraying the microparticles onto the polymeric network or dipping the polymeric network into a solution that includes the microparticles. The primed network 25 is applied to the expandable substrate 10 (step C) to form a "loaded" device 55. As used herein, the term "loaded device" means that the device includes microparticles 30 embedded within the polymeric network 20. In the embodiment shown in FIG. 2, the preformed polymeric network 20 is a substantially planar fibrous mat or sheet. However, other embodiments of a polymeric network 20 are possible, including networks have a more three dimensional structure, such as a hollow sheath or tube (not shown) configured to encompass the expandable substrate 10.

In another embodiment shown in FIG. 4, microparticles 30 are applied to the expandable substrate 10 (step B) to form a "primed" substrate 35. In this embodiment, it may be desirable to adhere the microparticles 30 to the expandable substrate 10 using a temporary adhesive configured to affix the microparticles 30 to the expandable substrate 10 during the fabrication process, but release the microparticles 30 when the device in vivo or when the device is in use. The release of the microparticles from the temporary adhesive can be due to differences in the surroundings or environment (e.g. in vivo versus during fabrication or storage) or due to the passage of time (e.g., due to dissolution or degradation of the adhesive) or due to the expansion of the substrate during use. Examples of temporary adhesives include biocompatible sugar-based adhesives, including but not limited to, trehalose, monosaccharides, or disaccharides. Other examples of temporary adhesives include, but are not limited to, biocompatible polymeric adhesives such as polyvinylpyrrolidone (PVP) and polyvinyl acetate (PVA). Once the primed substrate 35 is prepared, a polymeric network 20 is applied to the primed substrate 35 (step C) to form the "loaded device" 55 (step D). In the embodiment shown in FIG. 4, a "preformed" polymeric network 20 is applied to the primed substrate 35 to form the loaded device 55. As used herein, the term "preformed polymeric network" refers to a polymeric network that is fabricated, for example, by electrospinning, onto a surface other than the expandable substrate of the medical device. In the embodiment shown in FIG. 4, the preformed network 20 is a substantially planar fibrous mat or sheet. However, other embodiments of a polymeric network 20 are possible, including networks have more of a three dimensional structure, such as a hollow sheath or tube configured to encompass the expandable substrate 10 (not shown). Methods for adhering a preformed polymeric network 20 to a substrate are known and include, but are not limited to, the use of known biocompatible adhesives. In one embodiment, the polymeric network 20 can be adhered to the expandable substrate along the edges 27, 28 of the polymeric network 20. In another embodiment, the polymeric network 20 can be adhered to the expandable substrate 10 at any location between the edges 27, 28 of the polymeric network. In yet another embodiment (not shown), the polymeric network 20 is applied to the primed substrate 35 by an electrospinning process, in which polymeric fibers 22 are spun onto the primed substrate 35.

Expandable Medical Devices

Medical devices having an expanded and collapsed configuration are known and are used for a wide variety of purposes and can be constructed from a wide variety of materials. Although the discussion included herein focuses on the use of intravascular devices such as stents, balloon catheters, including plaque removing balloon catheters, and vascular occlusion devices, the technology is equally applicable to other non-vascular medical devices that have an expanded and a collapsed configuration, including, but not limited to expandable vertebral implants, such as those used to maintain intevertebral spacing and support the spine during vetebrectomy procedures; expandable intragastric devices, such as those used to induce a feeling of satiety or physical fullness of the stomach; and drainage catheters, such as those adapted to drain fluid from a body cavity which include an expandable retention member, wherein it may be desirable to have localized delivery of one or more therapeutic agents.

The exapandable medical device or substrate can be constructed from any suitable material, including both metal and non-metal materials and conductive or non-conductive materials. Examples of suitable biocompatible metals include, but are not limited to stainless steel, titanium, aluminum, zirconium, tantalum, nickel, molybdenum, niobium, cobalt, tungsten, platinum, palladium, gold, silver, copper chromium, vanadium, hafnium, zinc, iron and other metals, alloys or mixtures thereof. Examples of suitable non-metal materials include polymeric materials, for example, polystyrene, polycarbonate, polyester, polyethylene, polyethylene terephthalate (PET), polyglycolic acid (PGA), polyolefin, poly-(p-phenyleneterephthalamide), polyphosphazene, polypropylene, polytetrafluoroethylene, polyurethane, polyvinyl chloride, polyacrylate (including polymethacrylate), and silicone elastomers, as well as copolymers and combinations thereof.

In one embodiment, the expandable medical device includes a balloon catheter. A balloon catheter is a type of catheter having an inflatable "balloon" at its tip which is used during a catheterization procedure to enlarge a narrow opening or passage within the body. In general, the deflated balloon catheter is positioned, then inflated to perform the necessary procedure, and deflated again in order to be removed.

In the embodiment shown in FIG. 5, the balloon catheter 100 includes a flexible, elongate shaft 110 extending from a proximal end 120 to a distal end 130. The wall 111 of the shaft 110 defines a hollow passage or longitudinal lumen that extends along the center of the catheter 100. Near the distal end 130 of the shaft 110 is a balloon 140, which has a collapsed configuration (FIG. 5A) and an expanded configuration (FIG. 5B). The catheter 100 may also include a flexible guidewire 150, which is a thin wire used to guide the placement of the catheter 100.

In general, the distal end 130 of the shaft 110 is dimensioned to pass freely along a blood vessel in a human body. The catheter shaft 110 typically has an outside diameter greater than about 0.35 mm and less than about 0.88 mm. The proximal end 120 of the shaft 110 is adapted to extend outside the human body during use. The lumen is dimensioned to permit a guidewire 150 to pass through the lumen.

The diameter of the balloon 140 in the collapsed and expanded configuration can vary depending on the different vessels of the human (or animal) body in which the catheter 100 is used. Additionally, the size of the balloon 140 may vary depending upon the procedure in which it is to be used.

Polymeric Network

The implantable medical device described herein includes one or more layers of a polymeric network or scaffolding applied to at least a portion of the expandable substrate wherein one or more layers of polymeric network are configured to retain embedded microparticles when the device is in a collapsed configuration and to release microparticles when the device is in an expanded configuration. In one embodiment, the polymeric network is a woven or non-woven mesh of microfibers. In one embodiment, the polymeric network is fabricated using electrospinning technology, also called electrostatic spinning.

Electrospinning processes are known and include processes in which fibers with micron or sub-micron sized diameters are extruded from a polymeric network by an electrostatic potential. In an electrospinning process, a sufficiently high voltage is applied to a liquid droplet, which causes the liquid to become charged. In general, the liquid is subjected to a high voltage DC field, for example having a voltage of at least about 5 kV or having a voltage of less than about 30 kV. The electrostatic repulsion imparted by the high voltage counteracts the surface tension of the liquid and the droplet is stretched. When the electrostatic field is strong enough to overcome the surface tension of the liquid, the liquid droplet becomes unstable and a tiny jet is ejected from the surface of the droplet. This point of eruption is known as the Taylor cone. As the jet dries out in flight it is elongated by a whipping process caused by electrostatic repulsion until it is deposited on a grounded collector. As the jet reaches a grounded target, the material can be collected as an interconnected web containing relatively small diameter fibers and relatively small interstitial spaces between the fibers. The interstitial spaces between the fibers are referred to herein as "pores."

Several parameters of the electrospinning process can be altered to vary the physical, chemical and mechanical properties of the resulting network, including the thickness of the polymeric network, the diameter of the resulting fibers and the effective pore diameter of the resulting network. These parameters are known, and include, for example, (1) polymer type, (2) the viscosity of the polymer solution, (3) the conductivity of the polymer, (4) the electric potential used in the electrospinning process, (5) the spinneret size, (6) the distance to the collection area, (7) air temperature and humidity, (8) the polymer feed rate, (9) the relative motion between the spinneret and the collection area, (10) the pressure in the spin chamber, (11) the chemicals used to solubilized the polymers, and (12) polymer crystallinity.

Methods for determining polymer network morphology, including thickness, fiber diameter and effective pore diameter are known and include, but are not limited to, scanning electron microscopes (SEM), field emission SEM (FE-SEM) and transmission electron microscope (TEM).

The desired thickness of the polymeric network, fiber diameter and effective pore diameter can vary depending upon many factors, including the average diameter of microparticles to be embedded in the polymeric network, the size of the expandable substrate to which the network is applied and the relative difference between the collapsed and expanded configurations of the expandable substrate to which the network is applied. In one embodiment, the pore diameter of the polymeric network is at least about 25% greater in the expanded configuration as compared to the collapsed configuration, or at least about 50% greater, or at least about 100% greater. In one embodiment, the pore diameter in the expanded configuration is no more than about 500% greater than in the collapsed configuration, or no more than about 200% greater. In another embodiment, the polymeric network is constructed from a material or blend of material that ruptures when the device is in an expandable configuration to release the embedded microparticles. As use herein, the term "rupture" refers to a process in which at least some of the electrospun fibers of the polymeric network break, thereby forming one or more openings at one or more locations in the polymeric network that are sufficiently large to allow the release of microparticles from the polymeric network. In one embodiment, the tensile strength and/or elasticity of the polymeric fibers or blend of fibers is selected for properties such as elasticity and brittleness such that the fiber length cannot be increased more than about 25%, 50%, or 100% without at least some (e.g., at least about 10%, at least about 20%, at least about 30%, at least about 40%, at least about 50%, or up to 75%, up to 85%, up to 95%, up to 100%) of the fibers breaking.

If desired, the implantable medical device can include two or more polymeric network layers (as shown in FIG. 2). If desired, the different layers can have different mechanical, physical or chemical properties, including thickness, fiber diameter and effective pore diameter. For example, one polymeric network layer can have a thickness that is greater than or less than that of another polymeric network layer, or an effective pore diameter that is greater or less than the effective pore diameter of another layer, or an average fiber diameter that is greater or less than the average fiber diameter of another layer. In one embodiment, each polymeric network layer has a thickness of at least about 10 micrometers. In one embodiment, the fibers created by an electrospinning process may have diameters averaging less than about 200 micrometers, less than about 150 micrometers, or less than about 100 micrometers and more than about 1 micrometer, more than about 10 micrometers, or more than about 50 micrometers.

The desired effective pore diameter of the polymeric network when the expandable substrate is in a collapsed configuration (also called the first effective pore diameter) can vary depending upon the average diameter of embedded microparticle. In general, the first effective pore diameter of the polymeric network is less than the average diameter of the embedded microparticles. As discussed previously, the average pore diameter of the polymeric network can be greater than the average diameter of the embedded microparticles, but still retain most or all (e.g., at least about 50% or at least about 75%, and up to about 90% or up to about 100%) of the microparticles such that the effective pore diameter is considered to be smaller than the average pore diameter.

A wide variety of polymers and/or polymer compositions are suitable for use in electrospinning processes can include any biocompatible polymer or polymer composition including hydrophobic and hydrophilic polymers. Examples of suitable polymers include, but are not limited to, natural and recombinant proteins, polysaccharides, and degradable and non-degradable synthetic aliphatic and aromatic polymers. The polymer can be selected based upon its solubility properties with respect to a selected therapeutic agent, solvent, or emulsion system. In some instances, it may be desirable to have a polymeric network constructed from a material that reduces the likelihood of covalent and/or noncovalent interactions, such as covalent bonding of one or more structures present on the microparticle to one or more structures present in the network or non-covalent interactions such as hydrogen bonds, ionic bonds, Van der Waals forces, and hydrophobic interactions between the polymeric network and the embedded microparticles. While not wishing to be bound by theory, it is believed that decreasing the covalent and/or noncovalent interactions between the embedded microparticles and the polymeric network reduces the likelihood that the microparticles are retained within the polymeric network once the effective pore diameter of the network is greater than the average microparticle diameter. For example, in one embodiment, the polymeric network can be constructed from a hydrophobic material in which hydrophilic microparticles are embedded, such that the hydrophilic microparticles are not retained within the network when the pore diameter is increased. In other instances, it may be desirable to have a hydrophilic polymeric network in which hydrophobic microparticles are embedded, such that the hydrophobic microparticles are not retained within the network with the pore diameter is increased.

Non-limiting examples of suitable polymers for the polymeric network include poly(acrylate), poly(acrylamide), poly(esteramide), poly(styrene), poly(ethylene), poly(propylene), poly(urethane), poly(lactic acid), poly(glycolic acid), poly(ester), poly(alpha-hydroxy acid), poly($\epsilon$-caprolactone), poly(dioxanone), poly(orthoester), poly(ether-ester), poly(lactone), poly(carbonate), poly(phosphazene), poly(phosphanate), poly(ether), poly(anhydride), poly(glaxanone), poly(pyrolic acid), poly(phosphazenes), mixtures thereof and copolymers thereof.

Additional polymers that can be used in the polymeric network include, but are not limited to, polyalkylene polymers and copolymers, fluorocarbon polymers and copolymers, silicone polymers and copolymers. Still other polymers that can be used include, but are not limited to, polytetrafluoroethylenes, poly(tetrafluoroethylene-co-hexafluoropropenes), modified ethylene-tetrafluoroethylene copolymers, ethylene chlorotrifluoroethylene copolymers, polyvinylidene fluorides, polyethylene oxides, polyethylene terephthalates, and polyether block amides. In another embodiment, the polymer material can include one or more polymers, for example, polypyrrole, polyaniline, polythiophene, poly(p-phenylene vinylene), polyparalene, or a mixture thereof. In one embodiment, the polymer material can include poly(ethylene-vinyl acetate). In another embodiment, the polymer material can include one or more maltodextrane based polymers.

In yet another embodiment, the polymer material can include a mixture or combination of polymers. In one embodiment, the polymer material includes a combination of a first and a second polymer component. In one embodiment, the first polymer component is a poly(alkyl)(meth)acrylate. In another embodiment, the first polymer component is poly(butyl methacrylate). In another embodiment, the second polymer component is poly(ethylene-co-vinyl acetate). In another embodiment, the polymer component includes multi-block copolymers based on poly(ethylene glycol)(PEG) and poly(butylene terephthalate).

Microparticles

As used herein, the term "microparticles" refers to particles having an average diameter of less than about 0.5 mm, irrespective of the precise interior or exterior structure. Microparticles may be constructed from one or more materials, may be formed by using any processing technique, and may have any geometry, i.e., the microparticles can be generally spherical, octagonal or hexagonal and may be solid, hollow or porous, depending upon the desired application. Within the broad category of microparticles, "microspheres" refers to spherical microparticles and the subcategory of "microcapsules" applies to microparticles which have a core surrounded by a material which is different from that of the core. The core may be solid, liquid, or even gas. The terms "microparticle," "microsphere" and "microcapsule" are used interchangeably herein. In general, microparticles have a size greater than 0.1 μm and less than about 200 μm, or less than about 100 μm, less than about 50 μm, or less than about 25 μm. In general, a microparticle has a size between about 0.1 μm and 200 μm, or between about 0.5 μm and about 100 μm, or between about 1 μm and 25 μm. In general, particles with dimensions less than 0.1 μm are typically called nanoparticles.

The average diameter of the microparticles can vary depending upon many factors, including the effective pore diameter of the polymeric network. The relative sizes of the embedded microparticles and the pores of the polymeric network can vary, depending upon many factors, including the difference in the pore diameter when the expandable substrate is in a collapsed configuration and when the expandable substrate is in an expanded configuration. In general, the average diameter of the microparticles embedded in the polymeric network is greater than the effective pore diameter of the polymeric network when the expandable substrate is in a collapsed configuration. In one embodiment, the average diameter of the microparticles is between about 5 μm and about 10 μm and the effective pore diameter of the network in the collapsed configuration is between about 1 μm and about 5 μm and the effective pore diameter of the polymeric network in the expanded is at least 10 μm.

Microparticles are known and are commercially available. In one embodiment, one or more microparticles include only bioactive agent. In another embodiment, one or more microparticles include bioactive agent incorporated in a matrix or carrier. In another embodiment, one or more microparticles include bioactive agent incorporated in a time-release matrix. The microparticle matrix may be formed from any suitable biocompatible composition and include those made of glass, metals, polymers and other magnetic materials.

In one embodiment, the microparticles are biodegradable, also referred to herein as degradable. Degradable polymers can include natural and/or synthetic polymers. In one embodiment, the degradable polymer includes one or more hydrolytically unstable linkages in the polymeric backbone. Degradable polymers can include both those with bulk erosion characteristics and those with surface erosion characteristics. Biodegradable microparticles are known and include, but are not limited to, microparticles constructed from poly (lactic-co-glycolic Acid) (PLAGA); albumin-containing microparticles, microparticles of bovine serum albumin (BSA), and fibrinogen microparticles.

Synthetic degradable polymers can include: degradable polyesters (such as poly(glycolic acid), poly(lactic acid), poly (lactic-co-glycolic acid), poly(dioxanone), polylactones (e.g., poly(caprolactone)), poly(-hydroxybutyrate), poly(3-hydroxyvalerate), poly(valerolactone), poly(tartronic acid), poly(β-malonic acid), poly(propylene fumarate)); degradable polyesteramides; degradable polyanhydrides (such as poly(sebacic acid), poly(1,6-bis(carboxyphenoxy)hexane, poly(1,3-bis(carboxyphenoxy)propane); degradable polycarbonates (such as tyrosine-based polycarbonates); degradable polyiminocarbonates; degradable polyarylates (such as tyrosine-based polyarylates); degradable polyorthoesters; degradable polyurethanes; degradable polyphosphazenes; polyacetyls; polycyanoacrylates; polyetheresters; poly(alkylene alkylate); degradable polyurethanes; copolymers of polyethylene glycol and poly(lactide) or poly(lactide-co-glycolide); and blends and/or copolymers thereof. Additional polymeric materials that may be used to form microparticles include poly(ethylene oxide), poly(acrylic acid), poly(vinyl alcohol), poly(urethane), poly(N-isopropyl acrylamide), poly (vinyl pyrrolidone) (PVP), poly(methacrylic acid), poly(p-styrene carboxylic acid), poly(p-styrenesulfonic acid), poly (vinylsulfonicacid), poly(ethyleneimine), poly(vinylamine), poly(anhydride), poly(L-lysine), poly(L-glutamic acid), poly (gamma-glutamic acid), poly(ethylene), poly(propylene), poly(glycolide), poly(lactide-co-glycolide), poly(amide), poly(hydroxylacid), poly(sulfone), poly(amine), poly(saccharide), poly(HEMA), poly(anhydride), copolymers thereof, and blends thereof.

Specific examples of degradable polymers include poly (ether ester) multiblock copolymers based on poly(ethylene glycol) (PEG) and poly(butylene terephthalate) that can be described by the following general structure:

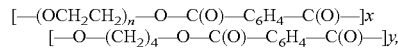

where —$C_6H_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. The subscript "n" can be selected such that the molecular weight of the PEG block is between about 300 and about 4000. The block copolymer can be engineered to provide a wide array of physical characteristics (e.g., hydrophilicity, adherence, strength, malleability, degradability, durability, flexibility) and active agent release characteristics (e.g., through controlled polymer degradation and swelling) by varying the values of n, x and y in the copolymer structure. Such degradable polymers can specifically include those described in U.S. Pat. No. 5,980,948, the content of which is herein incorporated by reference in its entirety.

Degradable polyesteramides can include those formed from the monomers OH-x-OH, z, and COOH-y-COOH, wherein x is alkyl, y is alkyl, and z is leucine or phenylalanine. Such degradable polyesteramides can specifically include those described in U.S. Pat. No. 6,703,040, the content of which is herein incorporated by reference in its entirety.

Degradable polymeric materials can also be selected from: (a) non-peptide polyamino polymers; (b) polyiminocarbonates; (c) amino acid-derived polycarbonates and polyarylates; and (d) poly(alkylene oxide) polymers.

In one embodiment, the degradable polymeric material includes a non-peptide polyamino acid polymer. In one embodiment, non-peptide polyamino acid polymers are described, for example, in U.S. Pat. No. 4,638,045 ("Non-Peptide Polyamino Acid Bioerodible Polymers," Jan. 20, 1987). Generally speaking, these polymeric materials are derived from monomers, including two or three amino acid units having one of the following two structures illustrated below:

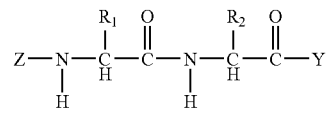

-continued

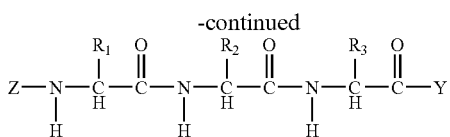

wherein the monomer units are joined via hydrolytically labile bonds at not less than one of the side groups $R_1$, $R_2$, and $R_3$, and where $R_1$, $R_2$, $R_3$ are the side chains of naturally occurring amino acids; Z is any desirable amine protecting group or hydrogen; and Y is any desirable carboxyl protecting group or hydroxyl. Each monomer unit includes naturally occurring amino acids that are then polymerized as monomer units via linkages other than by the amide or "peptide" bond. The monomer units can be composed of two or three amino acids united through a peptide bond and thus include dipeptides or tripeptides. Regardless of the precise composition of the monomer unit, all are polymerized by hydrolytically labile bonds via their respective side chains rather than via the amino and carboxyl groups forming the amide bond typical of polypeptide chains. Such polymer compositions are non-toxic, are degradable, and can provide zero-order release kinetics for the delivery of active agents in a variety of therapeutic applications. The amino acids can be selected from naturally occurring L-alpha amino acids, including alanine, valine, leucine, isoleucine, proline, serine, threonine, aspartic acid, glutamic acid, asparagine, glutamine, lysine, hydroxylysine, arginine, hydroxyproline, methionine, cysteine, cystine, phenylalanine, tyrosine, tryptophan, histidine, citrulline, ornithine, lanthionine, hypoglycin A, β-alanine, γ-amino butyric acid, a aminoadipic acid, canavanine, venkolic acid, thiolhistidine, ergothionine, dihydroxyphenylalanine, and other amino acids well recognized and characterized in protein chemistry.

Natural or naturally-based degradable polymers can include polysaccharides and modified polysaccharides such as starch, cellulose, chitin, chitosan, and copolymers thereof. Degradable polymers can specifically include polysaccharides such as those described in U.S. Publ. Pat. Application No. 2005/0255142, entitled "COATINGS FOR MEDICAL ARTICLES INCLUDING NATURAL BIODEGRADABLE POLYSACCHARIDES", U.S. Publ. Pat. Application No. 2007/0065481, entitled "COATINGS INCLUDING NATURAL BIODEGRADABLE POLYSACCHARIDES AND USES THEREOF", U.S. Publ. Pat. Application No. 20070218102, entitled "HYDROPHOBIC DERIVATIVES OF NATURAL BIODEGRADABLE POLYSACCHARIDES", and in U.S. Publ. Pat. Application No. 20070260054, entitled "HYDROPHOBIC DERIVATIVES OF NATURAL BIODEGRADABLE POLYSACCHARIDES", all of which are herein incorporated by reference in their entirety. Other natural or naturally based polymers can also include collagen; fibrin; gelatin; glycosaminoglycans (GAG); poly(hyaluronic acid); poly(sodium alginate); alginate; hyaluronan; agarose; polyhydroxybutyrate (PHB); copolymers thereof, and blends thereof.

Degradable polymers can include multi-block copolymers, including at least two hydrolysable segments derived from pre-polymers A and B, which segments are linked by a multi-functional chain-extender and are chosen from the pre-polymers A and B, and triblock copolymers ABA and BAB, wherein the multi-block copolymer is amorphous and has one or more glass transition temperatures (Tg) of at most 37° C. (Tg) at physiological (body) conditions. The pre-polymers A and B can be a hydrolysable polyester, polyetherester, polycarbonate, polyestercarbonate, polyanhydride or copolymers thereof, derived from cyclic monomers such as lactide (L,D or L/D), glycolide, ε-caprolactone, δ-valerolactone, trimethylene carbonate, tetramethylene carbonate, 1,5-dioxepane-2-one, 1,4-dioxane-2-one (para-dioxanone) or cyclic anhydrides (oxepane-2,7-dione). The composition of the pre-polymers may be chosen in such a way that the maximum glass transition temperature of the resulting copolymer is below 37° C. at body conditions. To fulfill the requirement of a Tg below 37° C., some of the above-mentioned monomers or combinations of monomers may be more preferred than others. This may by itself lower the Tg, or the pre-polymer is modified with a polyethylene glycol with sufficient molecular weight to lower the glass transition temperature of the copolymer. The degradable multi-block copolymers can include hydrolysable sequences being amorphous and the segments may be linked by a multifunctional chain-extender, the segments having different physical and degradation characteristics. For example, a multi-block co-polyester consisting of a glycolide-ε-caprolactone segment and a lactide-glycolide segment can be composed of two different polyester pre-polymers. By controlling the segment monomer composition, segment ratio and length, a variety of polymers with properties that can easily be tuned can be obtained. Such degradable multi-block copolymers can specifically include those described in U.S. Publ. App. No. 2007/0155906, the content of which is herein incorporated by reference in its entirety.

In another embodiment, the microparticles are biostable, also referred to herein as non-biodegradable. Suitable non-degradable polymers include natural and/or synthetic polymers. In one embodiment, the polymeric network is constructed from a non-degradable polymer composition that includes a plurality of polymers. In some embodiments, the active agents is adsorbed onto the surface of the biostable microparticle.

In one embodiment, the polymer composition includes a first polymer and a second polymer. Suitable first polymers can include a polymer selected from poly(alkyl(meth)acrylates) and poly(aromatic(meth)acrylates), where "(meth)" will be understood by those skilled in the art to include such molecules in either the acrylic and/or methacrylic form (corresponding to the acrylates and/or methacrylates, respectively). In one embodiment, the first polymer is poly(n-butyl methacrylate) (pBMA). Such polymers are available commercially, e.g., from Aldrich, with molecular weights ranging from about 200,000 Daltons to about 320,000 Daltons, and with varying inherent viscosity, solubility, and form (e.g., as crystals or powder). In some embodiments, poly(n-butyl methacrylate) (pBMA) is used with a molecular weight of about 200,000 Daltons to about 300,000 Daltons. In another embodiment, suitable first polymers can include poly(aryl (meth)acrylates), poly(aralkyl(meth)acrylates), and/or poly (aryloxyalkyl(meth)acrylates). Such terms are used to describe polymeric structures wherein at least one carbon chain and at least one aromatic ring are combined with acrylic groups, typically esters, to provide a composition. In one embodiment, polymeric structures include those with aryl groups having from 6 to 16 carbon atoms and with weight average molecular weights from about 50 to about 900 kilodaltons.

Suitable poly(aralkyl(meth)acrylates), poly(arylalky (meth)acrylates) or poly(aryloxyalkyl(meth)acrylates) can be made from aromatic esters derived from alcohols also containing aromatic moieties. Examples of poly(aryl(meth) acrylates) include poly(9-anthracenyl methacrylate), poly (chlorophenylacrylate), poly(methacryloxy-2-hydroxybenzophenone), poly(methacryloxybenzotriazole), poly (naphthylacrylate) and -methacrylate), poly(4-nitrophenyl acrylate), poly(pentachloro(bromo, fluoro) acrylate) and -methacrylate), and poly(phenyl acrylate) and -methacrylate). Examples of poly(aralkyl(meth)acrylates) include poly (benzyl acrylate) and -methacrylate), poly(2-phenethyl acrylate) and -methacrylate, and poly(1-pyrenylmethyl methacrylate). Examples of poly(aryloxyalkyl(meth)acrylates) include poly(phenoxyethyl acrylate) and -methacrylate), and poly(polyethylene glycol phenyl ether acrylates) and -methacrylates with varying polyethylene glycol molecular weights.

Poly(alkylene-co-alkyl(meth)acrylates) include those copolymers in which the alkyl groups are either linear or branched, and substituted or unsubstituted with non-interfering groups or atoms. In one embodiment, the alkyl groups include from 1 to 8 carbon atoms, inclusive or from 1 to 4 carbon atoms, inclusive. In another embodiment, the alkyl group is methyl. In some embodiments, copolymers that include such alkyl groups can include from about 15% to about 80% (wt) of alkyl acrylate. When the alkyl group is methyl, the polymer contains from about 20% to about 40% methyl acrylate in some embodiments, and from about 25% to about 30% methyl acrylate in a particular embodiment. When the alkyl group is ethyl, the polymer contains from about 15% to about 40% ethyl acrylate in an embodiment, and when the alkyl group is butyl, the polymer contains from about 20% to about 40% butyl acrylate in an embodiment.

Examples of suitable second polymers include poly(ethylene-co-vinyl acetate) (pEVA) having vinyl acetate concentrations of between about 10% and about 50% (12%, 14%, 18%, 25%, 33% versions are commercially available). The pEVA co-polymers with lower percent vinyl acetate become increasingly insoluble in typical solvents, whereas those with higher percent vinyl acetate become decreasingly durable.

In one embodiment, the polymeric composition includes a mixture of pBMA and pEVA. This mixture of polymers can be used with absolute polymer concentrations (i.e., the total combined concentrations of both polymers in the coating material), of between about 0.25 wt. % and about 99 wt. %. This mixture can also be used with individual polymer concentrations in the coating solution of between about 0.05 wt. % and about 99 wt. %. In one embodiment the polymer mixture includes pBMA with a molecular weight of from 100 kilodaltons to 900 kilodaltons and a pEVA copolymer with a vinyl acetate content of from 24 to 36 weight percent. In an embodiment the polymer mixture includes pBMA with a molecular weight of from 200 kilodaltons to 300 kilodaltons and a pEVA copolymer with a vinyl acetate content of from 24 to 36 weight percent. The concentration of the active agent or agents dissolved or suspended in the coating mixture can range from 0.01 to 99 percent, by weight, based on the weight of the final coating material. In another embodiment, second polymers can include one or more polymers selected from: (i) poly(alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers.

Alternatively, second polymers can include ethylene copolymers with other alkylenes, which in turn, can include straight and branched alkylenes, as well as substituted or unsubstituted alkylenes. Examples include copolymers prepared from alkylenes that include from 3 to 8 branched or linear carbon atoms, inclusive. In an embodiment, copolymers prepared from alkylene groups that include from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). In one embodiment, copolymers of this type can include from about 20% to about 90% (based on moles) of ethylene. In an embodiment, copolymers of this type include from about 35% to about 80% (mole) of ethylene. Such copolymers will have a molecular weight of between about 30 kilodaltons to about 500 kilodaltons. In one embodiment, copolymers are selected from the group consisting of poly (ethylene-co-propylene), poly(ethylene-co-1-butene), poly (ethylene-co-1-butene-co-1-hexene) and/or poly(ethylene-co-1-octene).

"Polybutenes" include polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. In an embodiment, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for instance it can contain up to 1000 ppm of an antioxidant (e.g., 2,6-di-tert-butyl-methylphenol). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Additional alternative second polymers include diolefin-derived, non-aromatic polymers and copolymers, including those in which the diolefin monomer used to prepare the polymer or copolymer is selected from butadiene ($CH_2$=CH—CH=$CH_2$) and/or isoprene ($CH_2$=CH—C($CH_3$)=$CH_2$). In an embodiment, the polymer is a homopolymer derived from diolefin monomers or is a copolymer of diolefin monomer with non-aromatic mono-olefin monomer, and optionally, the homopolymer or copolymer can be partially hydrogenated. Such polymers can be selected from the group consisting of polybutadienes prepared by the polymerization of cis-, trans- and/or 1,2-monomer units, or from a mixture of all three monomers, and polyisoprenes prepared by the polymerization of cis-1,4- and/or trans-1,4-monomer units. Alternatively, the polymer is a copolymer, including graft copolymers, and random copolymers based on a non-aromatic mono-olefin monomer such as acrylonitrile, and an alkyl(meth)acrylate and/or isobutylene. In an embodiment, when the mono-olefin monomer is acrylonitrile, the interpolymerized acrylonitrile is present at up to about 50% by weight; and when the mono-olefin monomer is isobutylene, the diolefin is isoprene (e.g., to form what is commercially known as a "butyl rubber"). In one embodiment, polymers and copolymers have a molecular weight between about 150 kilodaltons and about 1,000 kilodaltons. In an embodiment, polymers and copolymers have a molecular weight between about 200 kilodaltons and about 600 kilodaltons.

Additional alternative second polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$-$C_4$ alkyl(meth)acrylate (e.g., methyl methacrylate) and/or butene. Useful block copolymers include copolymer containing (a) blocks of polystyrene, (b) blocks of a polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt.) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional alternative second polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% (wt). In an embodiment, epichlorohydrin content is from about 50% to 100% (wt). In an embodiment, the epichlorohydrin-containing polymers have a molecular weight from about 100 kilodaltons to about 300 kilodaltons.

Non-degradable polymers can also include those described in U.S. Publ. Pat. App. No. 2007/0026037, entitled "DEVICES, ARTICLES, COATINGS, AND METHODS FOR CONTROLLED ACTIVE AGENT RELEASE OR HEMOCOMPATIBILITY", the contents of which are herein incorporated by reference in its entirety. As a specific example, non-degradable polymers can include random copolymers of butyl methacrylate-co-acrylamido-methyl-propane sulfonate (BMA-AMPS). In some embodiments, the random copolymer can include AMPS in an amount equal to about 0.5 mol. % to about 40 mol. %.

Matrix forming polymers can also include polymers including one or more charged group. For example, matrix forming polymers can include polymers with positively charged groups and/or negatively charged groups.

In one embodiment, the polymeric network includes one or more crosslinking compounds. In some instances, inclusion of one or more crosslinking compounds can increase durability of the polymeric network and/or help create a network with smaller pore sizes. In one embodiment, a mixture including microparticles, a polymeric component, and one or more crosslinking compounds can be prepared and treated to promote crosslinking and matrix formation prior to application to the expandable substrate. In another embodiment, a mixture that includes microparticles, a polymeric component and one or more crosslinking compounds can be applied to an expandable substrate and then treated to form the crosslinked matrix with entrapped microparticles. Suitable crosslinking compounds can be selected based on the properties of the polymeric materials and the entrapped microparticles. In one embodiment, the polymeric network can include one or more non-ionic photoactivatable cross-linking agents such as those described in U.S. Pat. Nos. 5,414,075 and 5,637,460 (Swan et al., "Restrained Multifunctional Reagent for Surface Modification"), the disclosure of which is herby incorporated by reference herein in its entirety. In another embodiment, the polymeric network can include one or more ionic photoactivatable cross-linking agents. Examples of ionic photoactivatable cross-linking agents can be found, for example, in U.S. Pat. No. 6,278,018, the disclosure of which is herby incorporated by reference herein in its entirety. In yet another embodiment, a non-photoreactive crosslinking agent can be included to promote the formation of crosslinked polymeric strands. A non-photoreactive agent can be added that can be a target for the photoreactive groups, that can initiate further polymerization of the polymers, or that can be a thermochemically activated crosslinker, for example a DSS(N,N-disuccinimidyl suberate) crosslinker.

Targeted Delivery of Microparticles

In one embodiment, the microparticles include one or more targeting agents. As used herein, the term "targeting agent" refers to a substance that increases the concentration of the microparticles at a targeted tissue, site or structure relative to other parts of the patient's body. In one embodiment, the targeting agent is a substance that selectively interacts with molecules present at the target site to increase the relative concentration of the microparticles at the target site. Targeting agents for microparticles are known and include the conjugation of one or more site-specific molecules to the particle surface or by constructing the microparticle from a material with an affinity to a specific tissue or site.

Targeting agents that can be coupled to the microparticles or included in the microparticle material, include, but are not limited to ligands, antibodies, including conjugated antibodies, carbohydrates, peptides, and lipoproteins. Examples of suitable targeting molecules include, but are not limited to Cell Adhesion Molecules (CAMs), such as lectins or selectins or antibodies specific thereto; oligopeptides such as integrins and integrin receptors; hormones, including peptide hormones; glycoproteins such as transferring and fibronectin; carbohydrates such as heparin; carrier proteins such as transcobalamin; growth factors, such as epidermal growth factors; plasma proteins such as albumin, globulins and fibrinogen; and extracellular matrix (ECM) molecules or ECM binding molecules. In some instances, the specificity-imparting partial structures of a targeting agent may be used.

In another embodiment, the targeting agent forms a part of the microparticle matrix. For example, in one embodiment, the microparticle polymeric matrix has an affinity to blood vessel endothelium. Examples of polymer matrices having an affinity to blood vessel endothelium include: PEG-containing polymers, or other mixed polyesteramide based polymers, and polyactive polymers.

Therapeutic Agent

In one embodiment, the microparticles are used as carriers for one or more therapeutic agents. As used herein, "therapeutic agent" includes any compound or bioactive agent having a therapeutic effect in an animal. The term "therapeutic agent" may be used interchangeably herein with the terms "drug", "pharmaceutically active agent" or "bioactive agent." In one embodiment, a single therapeutic agent is encapsulated within a single microparticle. In an alternate embodiment, two or more therapeutic agents can be encapsulated within a single microparticle. In yet another embodiment, two or more microparticles, each encapsulating one or more therapeutic agents can be combined.

Examples of suitable therapeutic agents include nucleic acids, polypeptides, or small molecule therapeutics and include, but are not limited to, anti-thrombotic agents, anti-proliferative agents, anti-inflammatory agents, anti-migratory agents, anti-restenosis agents, cytostatic compounds, toxic compounds, chemotherapeutic agents, agents affecting extracellular matrix production and organization, antineoplastic agents, anti-mitotic agents, anesthetic agents, analgesics, antimicrobials, antibiotics, anti-coagulants, vascular cell growth promoters, vascular cell growth inhibitors, cholesterol-lowering agents, vasodilating agents, TGF-β elevating agents, and agents that interfere with endogenous vasoactive mechanisms.

Examples of anti-proliferative agents include, but are not limited to, macrolide antibiotics including FKBP-12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Examples of anti-restenosis agents include, but are not limited to, paclitaxel, sirolimus, everolimus, tacrolimus, dexamethoasone, estradiol, trapidil, liprostin, Actinomycin D, Resten-NG, Ap-17, clopidogrel and Ridogrel.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. It should be readily apparent that any one or more of the design features described herein may be used in any combination with any particular configuration. With use of a molding process, such design features can be incorporated without substantial additional manufacturing costs. That the number of combinations are too numerous to describe, and the present invention is not limited by or to any particular illustrative combination described herein. The scope of the present subject matter should be determined with reference to the appended claims, along with the full scope of equivalents to which such claims are entitled.

What is claimed is:

1. An expandable medical device comprising:
   (a) an expandable substrate having a collapsed configuration and an expanded configuration;
   (b) a polymeric coating on the expandable substrate, wherein the polymeric coating forms a network attached to at least a portion of the expandable substrate, wherein the polymeric network includes polymeric fibers that define pores having a first effective pore diameter when the expandable substrate is in a collapsed configuration; and
   (c) microparticle carriers for one or more therapeutic agents, wherein the microparticles have an average diameter sufficient to be entrapped within the network when the expandable substrate is collapsed and wherein the microparticles are released from the network when the expandable substrate is in the expanded configuration, wherein at least some of the polymeric fibers are configured to rupture upon expansion of the device and release the microparticles.

2. The expandable medical device of claim 1, wherein the expandable substrate comprises an intravascular device.

3. The expandable medical device of claim 2, wherein the intravascular device is selected from the group consisting of: an angioplasty catheter, a stent and an occlusion device.

4. The expandable medical device of claim 1, wherein the first effective pore diameter is less than the average microparticle diameter.

5. The expandable medical device of claim 1, wherein the pore diameter of the polymeric network increases upon expansion of the expandable substrate to a second effective pore diameter and thereby releases the microparticles.

6. The expandable medical device of claim 5, wherein the second effective pore diameter of the network is greater than the first effective pore diameter.

7. The expandable medical device of claim 5, wherein the second effective pore diameter of the network is greater than the average microparticle diameter.

8. The expandable medical device of claim 1, wherein the polymeric network is constructed from a hydrophobic material and the microparticles comprise a hydrophilic material such that the microparticles are not retained within the network when the device is in the expanded configuration.

9. The expandable medical device of claim 1, further comprising a topcoat layer of a second polymeric network.

* * * * *